United States Patent
Liang et al.

(10) Patent No.: US 11,541,375 B2
(45) Date of Patent: Jan. 3, 2023

(54) OCM CATALYST COMPOSITION HAVING IMPROVED C2+ HYDROCARBON SELECTIVITY

(71) Applicants: SABIC Global Technologies B.V., Bergen op Zoom (NL); Wugeng Liang, Sugar Land, TX (US); David West, Sugar Land, TX (US); Hector Perez, Sugar Land, TX (US); Vidya Sagar Reddy Sarsani, Sugar Land, TX (US); Luanyi Elizabeth Li, Sugar Land, TX (US)

(72) Inventors: Wugeng Liang, Sugar Land, TX (US); David West, Sugar Land, TX (US); Hector Perez, Sugar Land, TX (US); Vidya Sagar Reddy Sarsani, Sugar Land, TX (US); Luanyi Elizabeth Li, Sugar Land, TX (US)

(73) Assignee: Sabic Global Technologies, B.V., Bergen op Zoom (NL)

( * ) Notice: Subject to any disclaimer, the term of this patent is extended or adjusted under 35 U.S.C. 154(b) by 0 days.

(21) Appl. No.: 17/623,042

(22) PCT Filed: Jul. 27, 2020

(86) PCT No.: PCT/US2020/043703
§ 371 (c)(1),
(2) Date: Dec. 27, 2021

(87) PCT Pub. No.: WO2021/030037
PCT Pub. Date: Feb. 18, 2021

(65) Prior Publication Data
US 2022/0258134 A1 Aug. 18, 2022

Related U.S. Application Data

(60) Provisional application No. 62/886,980, filed on Aug. 15, 2019.

(51) Int. Cl.
*B01J 23/30* (2006.01)
*C01F 17/32* (2020.01)
(Continued)

(52) U.S. Cl.
CPC ............. *B01J 23/30* (2013.01); *B01J 23/002* (2013.01); *B01J 23/10* (2013.01); *B01J 37/04* (2013.01);
(Continued)

(58) Field of Classification Search
CPC . B01J 23/30; B01J 23/002; B01J 23/10; B01J 37/04; B01J 37/088; C01F 17/32;
(Continued)

(56) References Cited

U.S. PATENT DOCUMENTS

| | | | |
|---|---|---|---|
| 4,918,257 A | 4/1990 | Murib | |
| 9,738,571 B2 * | 8/2017 | Schammel | ............... B01J 37/03 |
| 2016/0107143 A1 | 4/2016 | Schammel et al. | |

FOREIGN PATENT DOCUMENTS

| | | |
|---|---|---|
| WO | 2012162526 A2 | 11/2012 |
| WO | 2014143880 A1 | 9/2014 |

(Continued)

OTHER PUBLICATIONS

Filing Receipt and Specification of U.S. Appl. No. 62/886,980, filed Aug. 15, 2019, entitled "OCM Catalyst Composition Having Improved C2+ Hydrocarbon Selectivity," 44 pages.
(Continued)

*Primary Examiner* — Ali Z Fadhel
(74) *Attorney, Agent, or Firm* — Rodney B. Carroll; Conley Rose, P.C.

(57) ABSTRACT

The invention relates to a composition containing a catalyst suitable for producing ethylene and other $C_{2+}$ hydrocarbons at high selectivity while improving both methane conversion and product yield. Particularly, the catalyst contains mixed
(Continued)

metal oxides having at least one alkali earth metal and at least one rare earth metal along with an alkali metal promoter in the form of an alkali metal or in the form of an alkali metal tungstate. The invention further provides a method for preparing such a composition, using a calcination process to calcine the alkali metal promoters together with mixed metal oxides. Additionally, the invention further describes a process for producing $C_{2+}$ hydrocarbons, using such a composition.

20 Claims, 3 Drawing Sheets

(51) Int. Cl.
  *B01J 23/00* (2006.01)
  *B01J 23/10* (2006.01)
  *B01J 37/04* (2006.01)
  *B01J 37/08* (2006.01)
  *C01G 41/00* (2006.01)
  *C07C 2/84* (2006.01)
(52) U.S. Cl.
  CPC ............ *B01J 37/088* (2013.01); *C01F 17/32* (2020.01); *C01G 41/006* (2013.01); *C07C 2/84* (2013.01); *C01P 2002/50* (2013.01); *C07C 2523/10* (2013.01); *C07C 2523/30* (2013.01)
(58) Field of Classification Search
  CPC ..... C01G 41/006; C07C 2/84; C07C 2523/10; C07C 2523/30; C01P 2002/50
  See application file for complete search history.

(56) References Cited

FOREIGN PATENT DOCUMENTS

| WO | 2018164983 A1 | 9/2018 |
| WO | 2018175535 A1 | 9/2018 |
| WO | 2021030037 A1 | 2/2021 |

OTHER PUBLICATIONS

International Search Report and Written Opinion of International Application No. PCT/US2020/043703, dated Nov. 6, 2020, 9 pages.
Hiyoshi, Norihito et al., "Oxidative coupling of methane over alkali chloride-Mn—Na2WO4/SiO2 catalysts: Promoting effect of molten alkali chloride," Fuel Processing Technology, 2015, pp. 29-34, vol. 133, Elsevier B.V.

* cited by examiner

OCM CATALYST COMPOSITION HAVING IMPROVED C2+ HYDROCARBON SELECTIVITY

CROSS REFERENCE TO RELATED APPLICATION

This application is a filing under 35 U.S.C. 371 of International Application No. PCT/US2020/043703 filed Jul. 27, 2020, entitled "OCM Catalyst Composition Having Improved $C_{2+}$ Hydrocarbon Selectivity" which claims priority to U.S. Provisional Application No. 62/886,980 filed Aug. 15, 2019, which applications are incorporated by reference herein in their entirety.

FIELD OF INVENTION

The invention generally relates to the field of catalyst compositions used for the oxidative coupling of methane (OCM).

BACKGROUND

Methane is a widely available feedstock and if oxidatively coupled, in presence of certain methane coupling catalysts, commercially high value chemicals, such as ethylene and other $C_{2+}$ hydrocarbons, can potentially be produced at high production margins. However, oxidative coupling of methane has not been commercially exploited so far, as the desired $C_{2+}$ hydrocarbons such as ethylene, on being produced are more reactive than methane and tend to be oxidized to the more thermodynamically favored carbon oxides of CO and $CO_2$ ($CO_x$). As a consequence, selectivity towards $C_{2+}$ hydrocarbons, such as ethylene, is well below specific commercial requirements, which for certain application demand at least 80% ethylene selectivity. However, it has been observed that any attempts to increase the selectivity property of catalyst compositions have resulted in lowering of methane conversion and $C_{2+}$ hydrocarbon yields, leading to reduced process efficiency, and increased capital and operating expenditures.

Previous attempts to find suitable solutions for improving $C_{2+}$ hydrocarbon selectivity in OCM processes, have been described in various scientific and patent literature such as the teachings provided in the publication by Hiyoshi et. al (Oxidative coupling of methane over alkali chloride-Mn—$Na_2WO_4/SiO_2$ catalysts: Promoting effect of molten alkali chloride) or in the published patent application WO2014143880A1. Although the results appear promising, there is still room for further improvement in developing better and improved catalytic systems for the oxidative coupling of methane, having one or more benefits of having high $C_{2+}$ hydrocarbon selectivity along with improved methane conversion and $C_{2+}$ hydrocarbon yield.

SUMMARY

The invention relates to a composition, comprising a catalyst represented by a general formula (I): $(AM_zAE_aRE1_bRE2_cAT_dO_x)$ wherein, (i) 'AM' represents any one of an alkali metal or an alkali metal tungstate, wherein the alkali metal is selected from the group consisting of sodium, potassium, rubidium and caesium and wherein the alkali metal tungstate is selected from the group consisting of sodium tungstate, potassium tungstate, rubidium tungstate and caesium tungstate; (ii) 'AE' represents an alkaline earth metal; (iii) 'RE1' represents a first rare earth element; (iv) 'RE2' represents a second rare earth element; and (v) 'AT' represents a third rare earth element 'RE3', or a redox agent 'RX' selected from antimony, tin, nickel, chromium, molybdenum, tungsten, manganese, bismuth; wherein, 'a', 'b', 'c', 'd' and 'z' each independently represent relative molar ratio; wherein 'a' is 1.0; 'b' ranges from about 0.1 to about 10; 'c' ranges from 0 to about 10; 'd' ranges from 0 to about 10; 'z' ranges from about 0.01 to about 2; 'x' balances the oxidation state; wherein, the first rare earth element, the second rare earth element and the third rare earth element, are different; wherein further the catalyst is unsupported by silica. Further, it is understood by those skilled in art that where reference is made herein to balancing of the oxidation state with respect to the composition, the balancing is to achieve electro-neutrality of the overall composition containing the catalyst of the present invention. In some embodiments of the invention, the relative molar ratio 'z' ranges from about 0.3 to about 1. In some preferred embodiments of the invention, the relative molar ratio 'a' is 1.0, relative molar ratio 'b' is 0.5, relative molar ratio 'c' is 0.1 and the relative molar ratio 'd' is 0.3. In some preferred embodiments of the invention, the alkali metal is sodium. In some other preferred embodiments of the invention, the alkali metal tungstate is sodium tungstate.

In some embodiments of the invention, the alkaline earth metal 'AE' is selected from the group consisting of magnesium, calcium, strontium, barium, and combinations thereof. In some preferred embodiments of the invention, the alkaline earth metal 'AE', is strontium. In some other embodiments of the invention, the first rare earth element 'RE1', the second rare earth element 'RE2', and the third rare earth element 'RE3', are each independently selected from the group consisting of lanthanum, scandium, cerium, praseodymium, neodymium, promethium, samarium, europium, gadolinium, yttrium, terbium, dysprosium, holmium, erbium, thulium, ytterbium, lutetium, and combinations thereof. In some preferred embodiments of the invention, the alkaline earth metal 'AE' is strontium, the first rare earth element 'RE1' is lanthanum, the second rare earth element 'RE2' is neodymium, and the third rare earth element 'RE3' is erbium. In some preferred embodiments of the invention, the catalyst of formula (I) is represented by a general formula $Na_zSr_aLa_bNd_cEr_dO_x$, wherein 'a' is 1.0; 'z' ranges from about 0.3 to about 0.7; 'b' ranges from about 0.3 to about 1; 'c' ranges from greater than zero to about 0.3; and 'd' ranges from greater than zero to about 0.5. In some preferred embodiments of the invention, the catalyst of formula (I) is represented by the formula $Na_{0.3}Sr_{1.0}La_{0.5}Nd_{0.1}Er_{0.3}O_x$. In some preferred embodiments of the invention, the catalyst of formula (I) is represented by the formula $Na_{0.5}Sr_{1.0}La_{0.5}Nd_{0.1}Er_{0.3}O_x$.

In some aspects of the invention, the composition containing the catalyst of the present invention, has a $C_{2+}$ hydrocarbon selectivity ranging from about 82% to about 93% of total product formed, when the composition is used in a process for producing $C_{2+}$ hydrocarbon from methane and oxygen.

In some aspects of the invention, the composition containing the catalyst of the present invention, has a carbon oxide ($CO_x$) selectivity ranging from more than zero to about 18% of the total product formed, when the composition is used in a process for producing $C_{2+}$ hydrocarbon mixture product from methane and oxygen.

In some aspects of the invention, the invention provides a method for preparing the composition containing the catalyst of the present invention, the method comprising: (i) blending an alkali metal compound and a mixed metal oxide precursor and forming a catalyst precursor mixture, and (ii) calcining the catalyst precursor mixture at a temperature of at least 850° C. and for at least 5 hours and forming the composition. In some preferred embodiments of the invention, each of the mixed metal oxide precursor and the alkali metal compound, is independently calcined at a temperature of at least 300° C. and for at least 3 hours, prior to forming the catalyst precursor mixture.

In some embodiments of the present invention, the mixed metal oxide precursor and the alkali metal compound are dissolved in water to form an aqueous catalyst precursor solution prior to forming the catalyst precursor mixture. In some preferred embodiments of the invention, the alkali metal compound is a sodium salt. In some embodiments of the invention, the mixed metal oxide precursor comprises: a compound containing an alkaline earth metal 'AE' and at least one compound containing a first rare earth element 'RE1'. In some embodiments of the invention, the metal oxide precursor further comprises a compound containing a second rare earth element 'RE2' and a compound containing a third rare earth element 'RE3' or a redox agent 'RX'. In one aspect of the invention, the invention describes a process for preparing a $C_{2+}$ hydrocarbon mixture product comprising (a) introducing a feed mixture comprising methane and oxygen in a reactor containing the composition containing the catalyst of the present invention; (b) subjecting the feed mixture to a methane coupling reaction under conditions suitable to produce the $C_{2+}$ hydrocarbon mixture product; and (c) recovering the $C_{2+}$ hydrocarbon mixture product after removing unconverted methane from the $C_{2+}$ hydrocarbon mixture product. In some embodiments of the invention, the feed mixture has a methane to oxygen molar ratio ranging from about 2:1 to about 15:1.

Other objects, features and advantages of the invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from some specific embodiments may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which.

DETAILED DESCRIPTION

The invention is based, in part, on the discovery that a composition containing a catalyst, can be used for the oxidative coupling of methane with one or more benefits of having high $C_{2+}$ hydrocarbon selectivity along with improved methane conversion and $C_{2+}$ hydrocarbon yield. Advantageously, the catalyst composition of the present invention is formulated by calcining alkali metal promoters or alkali metal tungstate at specific proportion, with mixed metal oxides containing at least one rare earth metal and at least one alkaline earth metal, which enable the formulated catalyst composition to have high $C_{2+}$ hydrocarbon selectivity while improving both methane conversion and $C_{2+}$ hydrocarbon yield.

The following includes definitions of various terms and phrases used throughout this specification.

The terms "about" or "approximately" or "substantially" are defined as being close to as understood by one of ordinary skill in the art. In some non-limiting embodiments the terms are defined to be within 1%, preferably, within 0.1%, more preferably, within 0.01%, and most preferably, within 0.001%.

The terms "wt. %", "vol. %", or "mol. %" refers to a weight, volume, or molar percentage of a component, respectively, based on the total weight, the total volume, or the total moles of material that includes the component. In a non-limiting example, 10 moles of a particular component present in a 100 moles of a material is 10 mol. % of component. The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. The method of the invention can "comprise," "consist essentially of," or "consist of" particular ingredients, components, compositions, etc., disclosed throughout the specification. Any numerical range used through this disclosure shall include all values and ranges there between unless specified otherwise. For example, a boiling point range of 50° C. to 100° C. includes all temperatures and ranges between 50° C. and 100° C. including the temperature of 50° C. and 100° C.

The term "$C_{2+}$ hydrocarbon" or "$C_{2+}$ hydrocarbon mixture product" as used in this disclosure means the hydrocarbon products having at least two carbon atoms including ethylene, ethane, ethyne, propene, propane, and $C_4$-$C_5$ hydrocarbons, which are produced using the inventive composition containing the catalyst of the present invention. The term oxidative coupling of methane or "OCM" as referred or used throughout this disclosure means the oxidative coupling of methane or the reaction of methane and oxygen, for the production of $C_{2+}$ hydrocarbons from methane.

The term "methane conversion" as used throughout this disclosure means the amount of methane in terms of moles, which has undergone reaction with oxygen under oxidative coupling conditions. For the purposes of this invention, methane conversion can be measured by comparing the methane concentration at the outlet and inlet of an oxidative coupling of methane reactor, such a reactor being a 2.3 mm ID quartz tube reactor having a feed mixture flow rate adjusted from about 40 sccm and a catalyst loading of 20 mg.

The term "oxygen conversion" as used throughout this disclosure means the amount of oxygen in terms of moles which has undergone reaction with methane under oxidative coupling conditions. For the purposes of this invention, oxygen conversion can be measured by comparing the oxygen concentration at the outlet and inlet of an oxidative coupling of methane reactor, such a reactor being a 2.3 mm ID quartz tube reactor having a feed mixture flow rate adjusted from about 40 sccm and a catalyst loading of 20 mg.

The term "redox agent" as used herein means substances or elements capable of undergoing or promoting or supporting both oxidation or reducing reactions.

The term "selectivity" to a desired product or products refers to how much desired product was formed divided by the total products formed, both desired and undesired. For purposes of the disclosure herein, the selectivity to a desired product is a percentage selectivity based on moles converted into the desired product. Further, for purposes of the disclosure herein, a $C_x$ selectivity (e.g., $C_2$ selectivity, $C_{2+}$ selectivity, etc.) can be calculated by dividing a number of moles of carbon (C) from $CH_4$ that were converted into the desired product (e.g., $C_{C2C4}$, $C_{C2H6}$, etc.) by the total number of moles of C from $CH_4$ that were converted (e.g., $C_{C2C4}$, $C_{C2H6}$, $C_{C2H2}$, $C_{C3H6}$, $C_{C3H8}$, $C_{C4s}$, $C_{CO2}$, $C_{CO}$, etc.). $C_{C2C4}$=number of moles of C from $CH_4$ that were converted into $C_{2H4}$; $C_{C2H6}$=number of moles of C from $CH_4$ that were converted into $C_2H_6$; $C_{C2H2}$=number of moles of C from $CH_4$ that were converted into $C_2H_2$; $C_{C3H6}$=number of moles of C from $CH_4$ that were converted into $C_3H_6$; $C_{C3H8}$=number of moles of C from $CH_4$ that were converted into $C_3H_8$; $C_{C4s}$=number of moles of C from $CH_4$ that were converted into $C_4$ hydrocarbons ($C_4s$); $C_{CO2}$=number of moles of C from $CH_4$ that were converted into $CO_2$; $C_{CO}$=number of moles of C from $CH_4$ that were converted into CO; etc. Specifically, $C_{2+}$ hydrocarbon selectivity (e.g., selectivity to $C_{2+}$ hydrocarbons) refers to how much $C_{2H4}$, $C_3H_6$, $C_2H_2$, $C_2H_6$, $C_3H_8$, $C_5s$ and $C_4s$ were formed divided by the total product formed which includes $C_{2H4}$, $C_3H_6$, $C_2H_2$, $C_2H_6$, $C_3H_8$, $C_4s$, $C_5s$, $C_{n's}$, $CO_2$ and CO. Accordingly, a preferred way of calculating $C_{2+}$ hydrocarbon selectivity will be by using the equation:

$$\left(\frac{\begin{pmatrix}2C_{C2H4}+2C_{C2H6}+2C_{C2H2}+2C_{C3H6}+\\3C_{C3H8}+4C_{C4s}+5C_{C5s}+nC_{Cn's}\end{pmatrix}}{\begin{pmatrix}2C_{C2H4}+2C_{C2H6}+2C_{C2H2}+2C_{C3H6}+\\3C_{C3H8}+4C_{C4s}+5C_{C5s}+nC_{Cn's}+C_{CO2}+C_{CO}\end{pmatrix}}\right)\times100$$

Specifically, a high $C_{2+}$ hydrocarbon selectivity will signify increased formation of useful $C_{2+}$ hydrocarbon products over that of undesirable carbon oxide byproducts. The term "total product formed" used in the context of measuring selectivity includes $C_2H_4$, $C_3H_6$, $C_2H_2$, $C_2H_6$, $C_3H_8$, $C_4s$, $C_5s$, $C_{n's}$, $CO_2$ and CO.

The term "$C_{2+}$ hydrocarbon yield" is calculated by multiplying the methane conversion value at a particular oxygen conversion value with the $C_{2+}$ hydrocarbon selectivity obtained. The yield signifies the amount of useful $C_{2+}$ hydrocarbon mixture products formed when the feed is passed through an oxidative coupling of methane reactor. Higher the value of the $C_{2+}$ hydrocarbon yield, the more efficient and productive the catalytic process.

The invention provides for a composition, containing a catalyst comprising an alkali metal based promoter and a mixed metal oxide containing an alkaline earth metal and at least one rare earth metal. Particularly, in some aspects of the invention relates to a composition, comprising a catalyst represented by a general formula (I): $(AM_zAE_aRE1_bRE2_cAT_dO_x)$ wherein, (i) 'AM' represents any one of an alkali metal or an alkali metal tungstate, wherein the alkali metal is selected from the group consisting of sodium, potassium, rubidium and caesium and wherein the alkali metal tungstate is selected from the group consisting of sodium tungstate, potassium tungstate, rubidium tungstate and caesium tungstate; (ii) 'AE' represents an alkaline earth metal; (iii) 'RE1' represents a first rare earth element; (iv) 'RE2' represents a second rare earth element; and (v) 'AT' represents a third rare earth element 'RE3', or a redox agent 'RX' selected from antimony, tin, nickel, chromium, molybdenum, tungsten, manganese, bismuth; wherein, 'a', 'b', 'c', 'd' and 'z' each independently represent relative molar ratio; wherein 'a' is 1.0; 'b' ranges from about 0.1 to about 10, alternatively from about 0.3 to about 1, alternatively from about 0.4 to about 0.8; 'c' ranges from 0 to about 10, alternatively from about 0.3 to about 1, alternatively from about 0.4 to about 0.8; 'd' ranges from 0 to about 10, alternatively from about 0.3 to about 1, alternatively from about 0.4 to about 0.8; 'z' ranges from about 0.01 to about 2, alternatively from about 0.09 to about 1, alternatively from about 0.2 to about 0.8, alternatively from about 0.3 to about 0.7, alternatively from about 0.4 to about 0.6; 'x' balances the oxidation state; wherein, the first rare earth element, the second rare earth element and the third rare earth element, are different; and wherein further the catalyst is unsupported by silica. Specifically, the term "unsupported" as used herein means that the composition containing the catalyst of the present invention does not have silica as support but may in some embodiments of the invention include a support which is not of silica or in some embodiments of the invention may not contain a support at all. Further, it is understood by those skilled in art that, where reference is made herein to balancing of the oxidation state with respect to the composition, the balancing is to achieve electro-neutrality of the overall composition containing the catalyst of the present invention.

In some preferred embodiments of the invention, the alkali metal is sodium. In some other preferred embodiments of the invention, the alkali metal tungstate is sodium tungstate. The term "different" as used herein means that each of the rare earth elements are different chemical elements. In some embodiments of the invention, the relative molar ratio 'z' ranges from about 0.3 to about 1, alternatively from about 0.4 to about 0.8, alternatively from about 0.5 to about 0.8. In some preferred embodiments of the invention, the molar ratio 'a' is 1.0, molar ratio 'b' is 0.5, molar ratio 'c' is 0.1 and the molar ratio 'd' is 0.3.

In some embodiments of the invention, the alkaline earth metal 'AE' is selected from the group consisting of magnesium, calcium, strontium, barium, and combinations thereof. In some other embodiments of the invention, the first rare earth element 'RE1', the second rare earth element 'RE2', and the third rare element 'RE3', are each independently selected from the group consisting of lanthanum, scandium, cerium, praseodymium, neodymium, promethium, samarium, europium, gadolinium, yttrium, terbium, dysprosium, holmium, erbium, thulium, ytterbium, lutetium, and combinations thereof. In some preferred embodiments of the invention, the alkaline earth metal 'AE' is strontium, the first rare earth element 'RE1' is lanthanum, the second rare earth element 'RE2' is neodymium, and the third rare earth element 'RE3' is erbium. Without wishing to be limited by any specific theory, the incorporation of stable rare earth metal oxides imparts catalytic stability to the composition and mitigates risks of catalyst deactivation during the oxidative coupling reaction. In some preferred embodiments of the invention, the catalyst of formula (I) is represented by a general formula $Na_zSr_aLa_bNd_cEr_dO_x$, wherein 'a' is 1.0; 'z' ranges from about 0.3 to about 0.7; 'b' ranges from about 0.3 to about 1; 'c' ranges from greater than zero to about 0.3; and 'd' ranges from about greater than zero to about 0.5. In some preferred embodiments of the invention, the catalyst of formula (I) is represented by the formula $Na_{0.3}Sr_{1.0}La_{0.5}Nd_{0.1}Er_{0.3}O_x$. In some preferred embodiments of the invention, the catalyst of formula (I) is represented by the formula $Na_{0.5}Sr_{1.0}La_{0.5}Nd_{0.1}Er_{0.3}O_x$. In some other preferred embodiments of the invention, the catalyst of formula (I) is represented by the formula $((Na_2WO_4)_{0.5}Sr_{1.0}La_{0.5}Nd_{0.1}Er_{0.3}O_x)$. Further, without wishing to be bound by any specific theory and by way of this disclosure, it is believed that the synergistic combination of rare earth elements such as lanthanum, which promotes OCM catalyst activity, with rare earth element such as neodymium, which promotes $C_{2+}$ hydrocarbon selectivity, along with suitable proportion of alkali metal or alkali metal tungstate promoters, enables the composition containing the catalyst of the present invention, to demonstrate excellent selectivity, along with improved methane conversion and improved $C_{2+}$ hydrocarbon yield.

In some aspects of the invention, the invention provides a method for preparing the composition containing the catalyst of the present invention, the method comprises: (i) blending an alkali metal compound and a mixed metal oxide precursor and forming a catalyst precursor mixture, and (ii) calcining the catalyst precursor mixture at a temperature of at least 850° C., alternatively for at least 900° C., for at least 5 hours, or alternatively for at least 6 hours, and forming the composition containing the catalyst of the present invention. In some embodiments of the present invention, the mixed metal oxide precursor and the alkali metal compound are dissolved in water to form an aqueous catalyst precursor solution prior to forming the catalyst precursor mixture. In such embodiments of the invention, the alkali metal compound is an alkali metal salt. Non limiting examples of alkali metal salt includes alkali metal nitrates, alkali metal chlorides, alkali metal halides, alkali metal carbonates, alkali metal oxides. In some preferred embodiments of the invention, the alkali metal compound is a sodium salt. In some preferred embodiments of the invention, the alkali metal compound is sodium nitrate. Specifically, when the alkali metal compound is an alkali metal salt, the method of preparation of the composition containing the catalyst of the present invention involve steps of (a) blending the alkali metal compound with the mixed metal oxide precursor in distilled water to form an aqueous catalyst precursor; (b) drying the aqueous catalyst precursor overnight at a temperature of at least 110° C., alternatively at a temperature of at least 120° C., to form the catalyst precursor mixture containing the blended product of the alkali metal compound and the mixed metal oxide precursor; and thereafter (d) calcining the catalyst precursor mixture to obtain the composition containing the catalyst of the present invention.

In some other preferred embodiments of the invention, each of the mixed metal oxide precursor and the alkali metal compound, is independently calcined at a temperature of at least 300° C., alternatively at least 400° C. for at least 3 hours, prior to forming the catalyst precursor mixture. In some embodiments of the invention, the alkali metal compound is an alkali metal tungstate. In preferred embodiments of the invention, the alkali metal compound is sodium tungstate. Alternatively, when the alkali metal compound is an alkali metal tungstate, the method of preparation of the composition containing the catalyst of the present invention involve the steps of (a) obtaining the mixed metal oxide precursor by dissolving a mixture of metal oxide in water followed by drying overnight at a temperature of at least 110° C., alternatively at a temperature of at least 120° C., to form the mixed metal oxide precursor; (b) calcining the mixed metal oxide precursor at a temperature of at least 850° C., alternatively for at least 900° C., for at least 5 hours, or alternatively for at least 6 hours; (c) independently calcining the alkali metal compound at a temperature of at least 300° C.; (d) thereafter blending the calcined mixed metal oxide precursor with the calcined alkali metal compound, to form the catalyst precursor mixture; and subsequently (e) calcining the catalyst precursor mixture to obtain the composition containing the catalyst of the present invention.

In some embodiments of the invention, the mixed metal oxide precursor comprises: a compound containing an alkaline earth metal 'AE' and at least one compound containing a first rare earth element 'RE1'. In some embodiments of the invention, the metal oxide precursor further comprises a compound containing a second rare earth element 'RE2' and a compound containing a third rare earth element 'RE3' or a redox agent 'RX'. In some embodiments of the invention, the mixed metal precursor mixture comprises (i) a compound containing the alkaline earth metal (AE), (ii) a compound containing the first rare earth element (RE1), (iii) a compound containing the second rare earth metal (RE2), and (iv) a compound containing the third rare earth metal (RE3). Non-limiting examples of compounds used for preparing the mixed metal oxide precursor are nitrates, carbonates, acetates, halides, oxides, hydroxides and any combinations thereof. In some preferred embodiments of the invention, the compound chosen is a nitrate salt for each of alkaline earth metal (AE), the first rare earth element (RE1), the second rare earth element (RE2), the third rare earth element (RE3) and the redox agent. In some embodiments of the invention, the mixed metal oxide precursor is obtained by dissolving the nitrate salts of alkaline earth metal (AE), first rare earth element (RE1), second rare earth element (RE2), and third rare earth element (RE3), in water and followed by drying over night at a temperature of at least 120° C., to obtain the mixed metal oxide precursor.

In some aspects of the invention, a composition comprising a $C_{2+}$ hydrocarbon mixture product is formed using the composition of the present invention containing the catalyst of the present invention. In some aspects of the invention, $C_{2+}$ hydrocarbon mixture product comprises ethylene, ethane, ethyne, propene, propane, $C_4$-$C_5$ hydrocarbons, carbon dioxide, carbon monoxide and combinations thereof. In one aspect of the invention, the invention describes a process for preparing a $C_{2+}$ hydrocarbon mixture product comprising (a) introducing a feed mixture comprising methane and oxygen in a reactor containing the composition containing the catalyst of the present invention; (b) subjecting the feed mixture to a methane coupling reaction under conditions suitable to produce the $C_{2+}$ hydrocarbon mixture product; and (c) recovering the $C_{2+}$ hydrocarbon mixture product after removing unconverted methane from the $C_{2+}$ hydrocarbon mixture product. In some aspects of the invention, unconverted methane produced during the reaction, is removed from the $C_{2+}$ hydrocarbon mixture product. In some embodiments of the invention, the removal of unconverted methane from the $C_{2+}$ hydrocarbon mixture product is effected using a distillation column. In some embodiments of the invention, the distillation column is a cryogenic distillation column.

Methane coupling reaction under conditions suitable to produce $C_{2+}$ hydrocarbon mixture product include appropriate temperature conditions, pressure conditions to effect the coupling reaction. In some embodiments of the invention, the feed mixture comprising methane and oxygen may be preheated to a temperature ranging from about 500° C. to about 550° C., prior to introducing the feed mixture in the reactor for methane coupling. The reactor can comprise an adiabatic reactor, an autothermal reactor, an isothermal reactor, a tubular reactor, a cooled tubular reactor, a continuous flow reactor, a fixed bed reactor, a fluidized bed reactor, a moving bed reactor, and the like, or combinations thereof. In one preferred aspect of the invention, a 2.3 mm ID quartz tube reactor is used for the purposes of reacting oxygen with methane under conditions sufficient to affect the oxidative coupling of methane. In some aspects of the invention, the reactor can comprise an adiabatic reactor. In some aspects of the invention, the $C_{2+}$ hydrocarbon mixture product is produced at a reactor temperature ranging from about 600° C. to about 900° C., alternatively from about 650° C. to about 850° C., alternatively from about 700° C. to about 760° C. In some aspects of the invention, the reactor can comprise a catalyst bed comprising the composition capable of catalyzing the oxidative coupling of methane reaction. In some embodiments of the invention, the feed mixture has a methane to oxygen molar ratio ranging from about 2:1 to about 15:1, alternatively from about 4:1 to about 10:1, alternatively from about 5:1 to about 8:1. In some embodiments of the invention, the pressure in the reactor is maintained at a pressure sufficient to effect oxidative coupling of methane. The pressure may be maintained at a range of about 14.7 psi (ambient atmospheric pressure) to about 500 psi, alternatively at a range of about 14.7 psi (ambient atmospheric pressure) to about 200 psi, alternatively at a range of about 14.7 psi (ambient atmospheric pressure) to about 150 psi. In some embodiments of the invention, the feed mixture is introduced into the reactor at a gas hourly space velocity (GHSV) ranging from about 500 $h^{-1}$ to about 1,000,000 $h^{-1}$, alternatively from about 1,000 $h^{-1}$ to about 300,000 $h^{-1}$, alternatively from about 5,000 $h^{-1}$ to about 100,000 $h^{-1}$, alternatively from about 10,000 $h^{-1}$ to about 80,000 $h^{-1}$, alternatively from about 20,000 $h^{-1}$ to about 50,000 $h^{-1}$.

In some aspects of the invention, the composition containing the catalyst of the present invention, has a $C_{2+}$ hydrocarbon selectivity ranging from about 82% to about 93%, alternatively from about 83% to about 90%, alternatively from about 84% to about 86%, of total product formed, when the composition is used in a process for producing $C_{2+}$ hydrocarbon from methane and oxygen. The term "total product formed" used in the context of measuring selectivity includes the products formed of $C_{2H4}$, $C_3H_6$, $C_2H_2$, $C_2H_6$, $C_3H_8$, $C_4$s, $C_5$s, $C_{n's}$, $CO_2$ and CO. Without wishing to be bound by any specific theory, it is believed that such high selectivity towards $C_{2+}$ hydrocarbons, results in lowering the selectivity towards unwanted carbon oxide ($CO_x$) byproducts of carbon dioxide ($CO_2$) and carbon monoxide (CO). In some aspects of the invention, the composition containing the catalyst of the present invention, has a carbon oxide ($CO_x$) selectivity ranging from about 7% to about to about 18%, alternatively from about 10% to about 17%, or alternatively from about 14% to about 16%, of the total product formed, when the composition is used in a process for producing $C_{2+}$ hydrocarbon mixture product from methane and oxygen. In some aspects of the invention, the composition containing the catalyst of the present invention, has a $C_{2+}$ hydrocarbon selectivity ranging from about 4% to about 15%, alternatively from about 5% to about 10%, greater than $C_{2+}$ hydrocarbon selectivity of an alkali metal-free or an alkali metal tungstate free catalyst composition having the formula $(AE_aRE1_bRE2_cAT_dO_x)$ where (i) 'AE' represents an alkaline earth metal; (ii) 'RE1' represents a first rare earth element; (iii) 'RE2' represents a second rare earth element; and (iv) 'AT' represents a third rare earth element 'RE3', or a redox agent 'RX' selected from antimony, tin, nickel, chromium, molybdenum, tungsten, manganese, bismuth; wherein, 'a', 'b', 'c', and 'd' represents relative molar ratio; wherein 'a' is 1.0; 'b' ranges from about 0.1 to about 10, alternatively from about 0.3 to about 1, alternatively from about 0.4 to about 0.8; 'c' ranges from 0 to about 10, alternatively from about 0.3 to about 1, alternatively from about 0.4 to about 0.8; 'd' ranges from 0 to about 10, alternatively from about 0.3 to about 1, alternatively from about 0.4 to about 0.8; 'z' ranges from about 0.01 to about 2, alternatively from about 0.09 to about 1, alternatively from about 0.2 to about 0.8, alternatively from about 0.3 to about 0.7, alternatively from about 0.4 to about 0.6; 'x' balances the oxidation state; wherein, the first rare earth element, the second rare earth element and the third rare earth element, are different; and wherein further the catalyst composition is unsupported by silica.

The $C_{2+}$ hydrocarbon selectivity can be measured over a range of temperature ranging from about 600° C. to about 800° C. In a preferred embodiment of the invention, catalyst selectivity is measured at 750° C. Without wishing to be bound by any specific theory, it is believed that the synergistic combination of alkali metal or alkali metal tungstate promoters when calcined with mixed metal oxides, creates a catalyst composition having a unique structure and morphology, enabling high $C_{2+}$ hydrocarbon selectivity along with improved methane conversion and yield. Further it is believed, that for the present invention, the absence of a catalyst support such as silica, enables promoter loading to be tuned as per requirement and enables improved selectivity and methane conversion.

The selectivity property exhibited by the inventive catalyst composition, results in lowering of the overall heat produced during the coupling reaction, improving catalyst performance and aiding in controlling reactor operations. Further, as may be appreciated by a person skilled in the art, the selectivity and methane conversion properties of an OCM catalyst are generally of opposing attributes. In some aspects of the invention and as evidenced from the results of Example 1, the inventors surprisingly found that the composition containing the catalyst of the present example, demonstrates excellent $C_{2+}$ hydrocarbon selectivity along with improved methane conversion. In one aspect of the invention, methane conversion ranges from about 5% to about 20%, alternatively from about 8% to about 16%, of the total number of moles of methane present in the feed mixture and when measured at various levels of oxygen conversion from about 3% oxygen conversion to about 100% oxygen conversion, during the OCM reaction. The methane conversion can be measured by using methane concentration using a gas chromatograph. The methane conversion can be determined using the equation: ($CH_4$ (inlet) —$CH_4$ (outlet)/$CH_4$ (inlet))×100, where $CH_4$ (inlet) is the concentration of methane in terms of moles, at the inlet of the reactor and $CH_4$ (outlet) is the concentration of methane, in terms of moles, at the outlet. For the purposes of this invention, methane conversion can be measured by comparing the methane concentration at the outlet and the inlet of an oxidative coupling of methane reactor, such a reactor being a 2.3 mm ID quartz tube reactor having a feed mixture flow rate adjusted from about 40 sccm and a catalyst loading of 20 mg.

Particularly in some aspects of the invention, the composition containing the catalyst of the present invention when used in an OCM process, results in improved methane conversion and improved $C_{2+}$ hydrocarbon yield compared to catalyst compositions (control compositions) having similar compositions but without alkali metal or alkali metal tungstate promoters. In some aspects of the invention, the process for preparing the $C_{2+}$ hydrocarbon mixture product using the composition comprising the catalyst of the present invention, has a methane conversion of about 5% to about 25%, alternatively of about 10% to about 20%, alternatively of about 12% to about 18%, greater than the methane conversion obtained from a process using an alkali metal-free or an alkali metal tungstate free catalyst composition, having a formula ($AE_aRE1_bRE2_cAT_dO_x$) where (i) 'AE' represents an alkaline earth metal; (ii) 'RE1' represents a first rare earth element; (iii) 'RE2' represents a second rare earth element; and (iv) 'AT' represents a third rare earth element 'RE3', or a redox agent 'RX' selected from antimony, tin, nickel, chromium, molybdenum, tungsten, manganese, bismuth; wherein, 'a', 'b', 'c', and 'd' represents relative molar ratio; wherein 'a' is 1.0; 'b' ranges from about 0.1 to about 10, alternatively from about 0.3 to about 1, alternatively from about 0.4 to about 0.8; 'c' ranges from 0 to about 10, alternatively from about 0.3 to about 1, alternatively from about 0.4 to about 0.8; 'd' ranges from 0 to about 10, alternatively from about 0.3 to about 1, alternatively from about 0.4 to about 0.8; 'z' ranges from about 0.01 to about 2, alternatively from about 0.09 to about 1, alternatively from about 0.2 to about 0.8, alternatively from about 0.3 to about 0.7, alternatively from about 0.4 to about 0.6; 'x' balances the oxidation state; wherein, the first rare earth element, the second rare earth element and the third rare earth element, are different; and wherein the catalyst composition is unsupported by silica.

In some aspects of the invention, the process for preparing the $C_{2+}$ hydrocarbon mixture product using the composition comprising the catalyst of the present invention, has a $C_{2+}$ hydrocarbon yield of about 10% to about 60%, alternatively of about 15% to about 50%, alternatively of about 20% to about 40%, greater than the $C_{2+}$ hydrocarbon yield obtained from a process using an alkali metal-free or an alkali metal tungstate free catalyst composition, having a formula ($AE_aRE1_bRE2_cAT_dO_x$) where (i) 'AE' represents an alkaline earth metal; (ii) 'RE1' represents a first rare earth element; (iii) 'RE2' represents a second rare earth element; and (iv) 'AT' represents a third rare earth element 'RE3', or a redox agent 'RX' selected from antimony, tin, nickel, chromium, molybdenum, tungsten, manganese, bismuth; wherein, 'a', 'b', 'c', and 'd' represents relative molar ratio; wherein 'a' is 1.0; 'b' ranges from about 0.1 to about 10, alternatively from about 0.3 to about 1, alternatively from about 0.4 to about 0.8; 'c' ranges from 0 to about 10, alternatively from about 0.3 to about 1, alternatively from about 0.4 to about 0.8; 'd' ranges from 0 to about 10, alternatively from about 0.3 to about 1, alternatively from about 0.4 to about 0.8; 'z' ranges from about 0.01 to about 2, alternatively from about 0.09 to about 1, alternatively from about 0.2 to about 0.8, alternatively from about 0.3 to about 0.7, alternatively from about 0.4 to about 0.6; 'x' balances the oxidation state; wherein, the first rare earth element, the second rare earth element and the third rare earth element, are different; and wherein the catalyst composition is unsupported by silica. Without wishing to be limited by any theory, it is suspected that the significantly higher $C_{2+}$ hydrocarbon selectivity and improved methane conversion along with limited oxygen availability in the feed mixture compared to methane, results in higher methane conversion and higher $C_{2+}$ hydrocarbon yield compared to control composition.

Accordingly, the invention includes various embodiments related to catalyst compositions that exhibit one or more benefits of having high $C_{2+}$ hydrocarbon selectivity, with improved methane conversion and $C_{2+}$ hydrocarbon yield.

Specific examples demonstrating some of the embodiments of the invention are included below. The examples are for illustrative purposes only and are not intended to limit the invention. It should be understood that the embodiments and the aspects disclosed herein are not mutually exclusive and such aspects and embodiments can be combined in any way. Those of ordinary skill in the art will readily recognize parameters that can be changed or modified to yield essentially the same results.

EXAMPLES

Example 1

Catalyst composition having the formula ($Na0.5Sr1.0La0.5Nd0.1Er0.3O_x$) formed by using sodium salt precursor.

Purpose: Example 1 demonstrates the preparation and use of a composition comprising an alkali metal promoted catalyst, having the formula ($Na_{0.5}Sr_{1.0}La_{0.5}Nd_{0.1}Er_{0.3}O_x$). The incorporation of sodium in the catalyst composition is achieved by using a sodium nitrate salt as the precursor material. The composition is used for the production of $C_{2+}$ hydrocarbon mixture product at high selectivity with improved methane conversion and product yield. The performance of the inventive catalyst composition of Example 1 in terms of $C_{2+}$ hydrocarbon selectivity, methane conversion and $C_{2+}$ hydrocarbon yield is further compared with a control containing a catalyst composition, which is free of sodium metal promoter.

Materials: The following materials are procured and used for the synthesis of the composition.

TABLE 1

Inventive catalyst composition ($Na_{0.5}Sr_{1.0}La_{0.5}Nd_{0.1}Er_{0.3}O_x$)

| Catalyst composition: $AM_zAE_aRE1_bRE2_cAT_dO_x$ | Element/ Compound used | Relative molar ratio | Precursor Material | Supplier |
|---|---|---|---|---|
| AM | Sodium (Na) | z = 0.5 | Sodium Nitrate $Na(NO_3)$ | Sigma-Aldrich |
| AE | Strontium (Sr) | a = 1.0 | Strontium Nitrate: $Sr(NO_3)_2$ | Sigma-Aldrich |
| RE1 | Lanthanum (La) | b = 0.5 | Lanthanum Nitrate $La(NO_3)_3 \cdot 6H_2O$ | Sigma-Aldrich |
| RE2 | Neodymium (Nd) | c = 0.1 | Neodymium Nitrate: $Nd(NO_3)_3 \cdot 6H_2O$ | Sigma-Aldrich |
| AT = RE3 | Erbium (Er) | d = 0.3 | Erbium Nitrate $Er(NO_3)_3 \cdot 6H_2O$ | Sigma-Aldrich |

Method for preparing the composition containing the inventive catalyst of Example 1 ($Na_{0.5}Sr_{1.0}La_{0.5}Nd_{0.1}Er_{0.3}O_x$): The composition containing the catalyst of Example 1, was prepared by a general method of (i) blending an alkali metal compound and a mixed metal oxide precursor and forming a catalyst precursor mixture, and (ii) calcining the catalyst precursor at a temperature of at least 850° C. for at least 5 hours and forming the composition containing the catalyst of Example 1. The mixed metal oxide precursor and the alkali metal compound were blended and dissolved in water to form an aqueous catalyst precursor solution prior to forming the catalyst precursor mixture.

More specifically, the method included the step of obtaining the mixed metal oxide precursor containing 8.47 g of strontium nitrate ($Sr(NO_3)_2$), 8.66 g of lanthanum nitrate ($La(NO_3)_{3.6}H_2O$), 1.76 g of neodymium nitrate ($Nd(NO_3)_{3.6}H_2O$) and 5.32 g of erbium nitrate ($Er(NO_3)_{3.6}H_2O$). The mixed metal oxide precursor was taken in a crucible and then blended with the alkali metal compound in the form of 0.34 g of sodium nitrate ($Na(NO_3)$), and subsequently dissolved in 80 ml of distilled water to form the aqueous catalyst precursor solution. The aqueous catalyst precursor solution was subsequently dried overnight at 120° C. to form the catalyst precursor mixture. The catalyst precursor mixture was then calcined at 900° C. for 6 hours to obtain the inventive catalyst composition of Example 1. The catalyst composition so obtained was crushed and the catalyst performance was evaluated. A reference catalyst composition (Reference 1) to be used as a control to the inventive composition of Example 1 was also prepared as described below:

Method for preparing the Reference 1 catalyst composition having the formula ($Sr_{1.0}La_{0.5}Nd_{0.1}Er_{0.2}O_x$): The following steps were followed for the synthesis of Reference 1 composition: 8.46 g of strontium nitrate ($Sr(NO_3)_2$), 8.66 g of lanthanum nitrate ($La(NO_3)_{3.6}H_2O$) and 1.75 g of neodymium nitrate ($Nd(NO_3)_{3.6}H_2O$) were mixed and dissolved in 42 ml of distilled water to form a solution. The solution was subsequently dried overnight at a temperature of 125° C. followed by calcination at 900° C. for 6 hours to obtain the control composition of Reference 1. The Reference 1 composition was then crushed and tested for its performance. A Reference 2 catalyst composition was also prepared having the formula $Sr_{1.0}La_{0.5}Nd_{0.1}Er_{0.3}O_x$, and having a composition identical to Reference 1 catalyst composition except a minor difference in the relative amount of Erbium. As evidenced from the selectivity data from Table 3, Reference 1 and Reference 2 catalyst compositions, have similar composition and similar levels of $C_{2+}$ hydrocarbon selectivity and would serve as a suitable control for evaluating the performance of Example 1.

Figure 1:
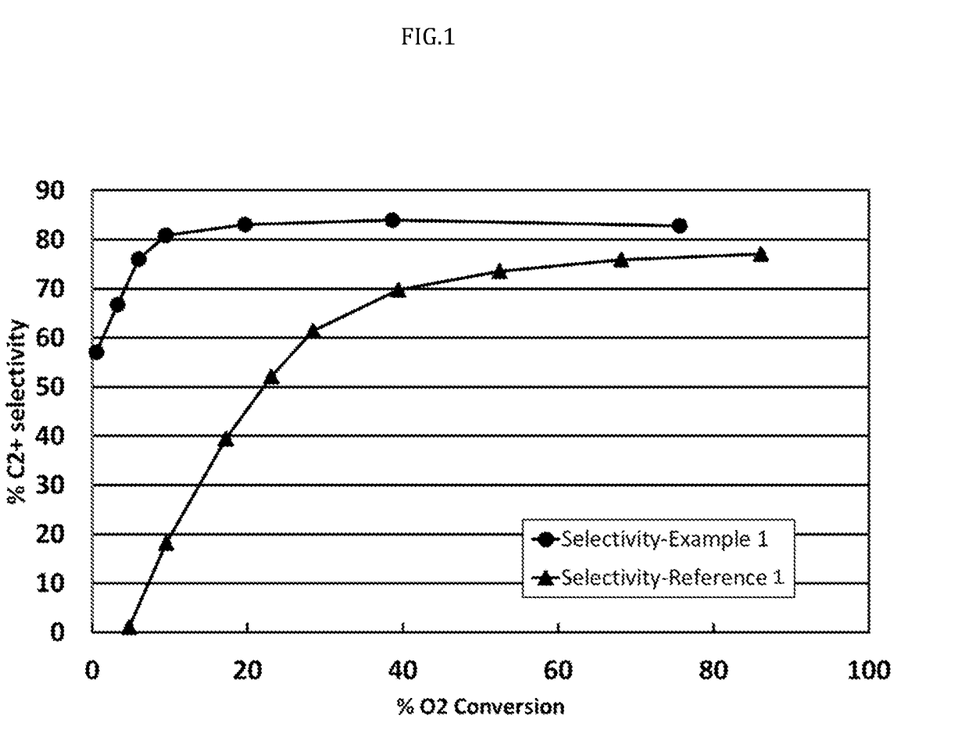
FIG. 1 is a graphical representation of the $C_{2+}$ hydrocarbon selectivity of inventive Example 1 measured at various levels of oxygen conversion and compared with the $C_{2+}$ hydrocarbon selectivity of Reference 1 catalyst composition.
Figure 2:
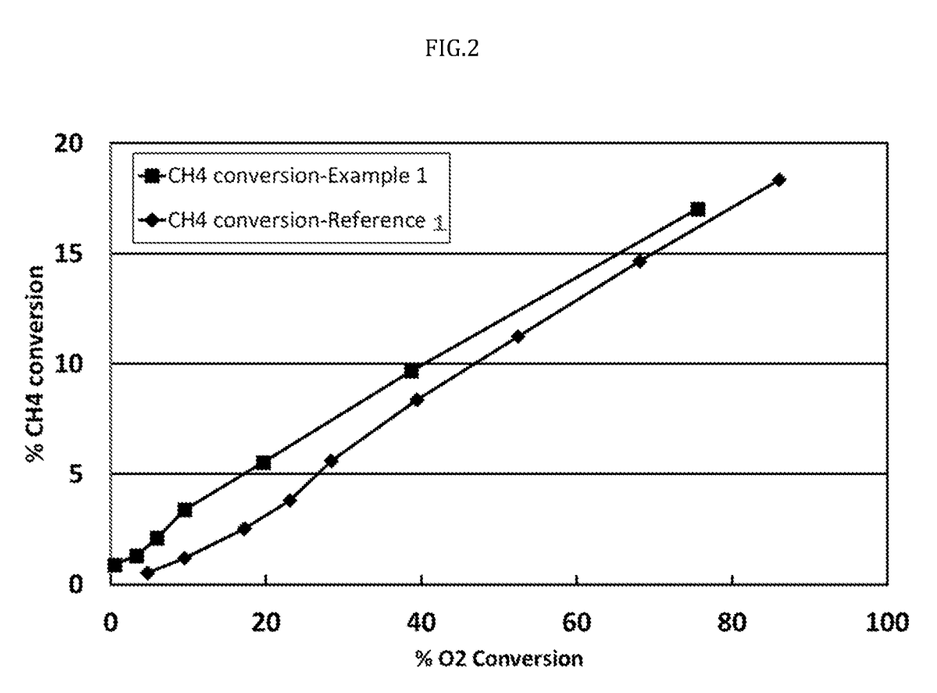
FIG. 2 is a graphical representation of methane conversion measured at various levels of oxygen conversion of the inventive catalyst composition prepared under Example 1 and compared with the methane conversion of Reference 1 catalyst composition.
Figure 3:
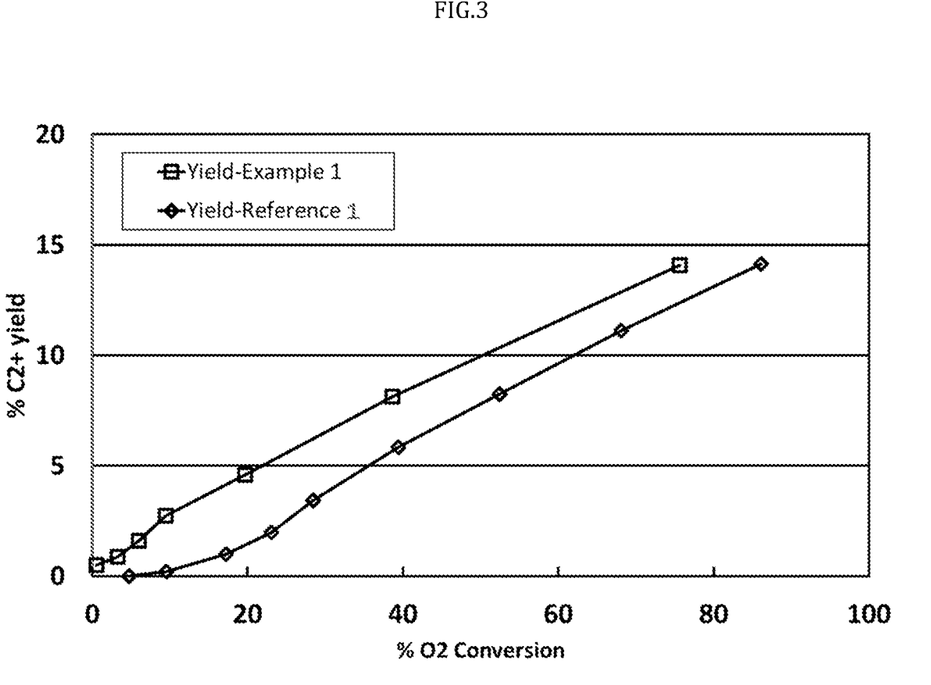
FIG. 3 is a graphical representation of $C_{2+}$ hydrocarbon yield of inventive Example 1 measured at various levels of oxygen conversion and compared with Reference 1 catalyst composition.

Process for producing $C_{2+}$ hydrocarbon mixture product using the composition of Example 1: The composition obtained from the practice of Example 1, was thereafter used for producing $C_{2+}$ hydrocarbon mixture product using the process comprising (a) introducing a feed mixture comprising methane and oxygen in a reactor containing the inventive composition of Example 1; (b) subjecting the feed mixture to a methane coupling reaction under conditions suitable to produce the $C_{2+}$ hydrocarbon mixture product; and (c) recovering the $C_{2+}$ hydrocarbon mixture product after removing unconverted methane from the $C_{2+}$ hydrocarbon mixture product. More particularly, the composition containing the catalyst obtained from Example 1, was placed in a 2.3 mm ID quartz tube, and was contacted with a feed mixture containing methane and oxygen. The ratio of methane to oxygen was adjusted to a molar ratio of 7.4:1 and the feed mixture flow rate was adjusted from 40 sccm. The catalyst loading in the reactor was 20 mg. The $C_{2+}$ hydrocarbon mixture product so obtained was analyzed using online Gas Chromatograph, Agilent 7890 GC, having a thermal conductivity detector (TCD) and a flame ionization detector (FID). The performance of the inventive catalyst composition of Example 1, in terms of $C_{2+}$ hydrocarbon selectivity, methane conversion and $C_{2+}$ hydrocarbon yield was measured across a range of methane conversion or oxygen conversion values, during the course of OCM reaction, at a reactor temperature of 750° C. The catalyst composition of Reference 1 and Reference 2 were subjected to identical reaction conditions and process steps as that of the inventive composition of Example 1. For the purpose of measuring and comparing the selectivity performance of the inventive composition of Example 1 with that of Reference 1 catalyst composition, the maximum $C_{2+}$ hydrocarbon selectivity and minimum $CO_x$ selectivity was noted. FIG. 1, illustrates the $C_{2+}$ hydrocarbon selectivity across a range oxygen conversion values. Similarly, as shown by way of FIG. 2 and FIG. 3 the methane conversion performance and the $C_{2+}$ hydrocarbon yield of the inventive catalyst, was measured across a range of oxygen conversion values and the value was noted at a specific oxygen conversion value such as 40% oxygen conversion for meaningful comparison with the performance of the control (Reference 1 catalyst composition).

The operating parameters for producing the $C_{2+}$ hydrocarbon mixture product is as given below:

TABLE 2

Operating Parameter used for producing $C_{2+}$ hydrocarbon mixture product

| Pressure inside reactor (psi) | Gas Hourly Space Velocity (GHSV) (hr$^{-1}$) | Reactor Temperature at which Selectivity is measured |
|---|---|---|
| Ambient pressure, (14.7) | 115,589 | 750° C. |

Results: The catalyst performance obtained using the catalyst composition of Example 1 is compared with the performance of Reference 1 and Reference 2 and tabulated below.

TABLE 3

Catalyst selectivity/Methane conversion/Yield ($Na_{0.5}Sr_{1.0}La_{0.5}Nd_{0.1}Er_{0.3}O_x$)

| | Maximum $C_{2+}$ hydrocarbon selectivity | Minimum carbon oxide ($CO_X$) selectivity | Methane conversion measured at 40% oxygen ($O_2$) conversion | Yield (%) obtained |
|---|---|---|---|---|
| Inventive composition Example 1 | 85.4 | 14.6 | 9.9 | 7.8 |
| (Control) Reference 1 - $Sr_{1.0}La_{0.5}Nd_{0.1}Er_{0.2}O_x$ | 79.8 | 20.2 | 8.5 | 5.6 |
| (Control) Reference 2 $Sr_{1.0}La_{0.5}Nd_{0.1}Er_{0.3}O_x$ | 79.7 | 20.3 | NA | NA |

The results from Table 3 indicate that inventive catalyst composition of Example 1, demonstrates over 7% improvement in the $C_{2+}$ hydrocarbon selectivity compared to the $C_{2+}$ hydrocarbon selectivity of both control references Reference 1 and Reference 2 catalyst compositions. Accordingly, the inventive catalyst demonstrates reduced selectivity towards carbon oxide byproducts ($CO_X$). Further, as evidenced from FIG. 1, the inventive catalyst composition of Example 1, demonstrates improved $C_{2+}$ hydrocarbon selectivity across a broad range of oxygen conversion. The increased selectivity towards the more useful $C_{2+}$ hydrocarbon products over that of carbon oxide byproducts ($CO_X$), is particularly beneficial in improving product yield and improving the overall OCM process efficiency.

As is evident from Table 3, at 40% oxygen conversion, methane conversion performance of the inventive catalyst composition of Example 1, demonstrates about 16% increase in methane conversion and nearly 40% increase in $C_{2+}$ hydrocarbon yield compared to the methane conversion and $C_{2+}$ hydrocarbon yield performance of the Reference 1 composition. However, from FIG. 2 and FIG. 3, it is evident that the inventive composition of Example 1 has improved methane conversion and improved $C_{2+}$ hydrocarbon yield compared to Reference 1 catalyst composition, across a broad range of oxygen conversion values and not just limited to 40% oxygen conversion value.

Example 2

Catalyst Composition Having the Formula ($Na_{0.3}Sr_{1.0}La_{0.5}Nd_{0.1}Er_{0.3}O_x$) Formed by Using Sodium Salt Precursor.

Purpose: Example 2 demonstrates the preparation and use of a composition comprising an alkali metal promoted catalyst, having the formula ($Na_{0.3}Sr_{1.0}La_{0.5}Nd_{0.1}Er_{0.3}O_x$). The incorporation of sodium in the catalyst composition is achieved by using a sodium nitrate salt as the precursor material. The performance of the inventive catalyst composition of Example 2 is compared with a control (Reference 1 and Reference 2 catalyst composition) containing a catalyst composition, which is free of sodium metal promoter.

Materials: The following materials are procured and used for the synthesis of the composition.

TABLE 4

Inventive catalyst composition ($Na_{0.3}Sr_{1.0}La_{0.5}Nd_{0.1}Er_{0.3}O_x$)

| Catalyst composition: AMzAEaRE1bRE2cATdOx | Element/ Compound used | Relative molar ratio | Precursor Material | Supplier |
|---|---|---|---|---|
| AM | Sodium (Na) | z = 0.3 | Sodium Nitrate Na(NO$_3$) | Sigma-Aldrich |
| AE | Strontium (Sr) | a = 1.0 | Strontium Nitrate: Sr(NO$_3$)$_2$ | Sigma-Aldrich |
| RE1 | Lanthanum (La) | b = 0.5 | Lanthanum Nitrate La(NO$_3$)$_3$•6H$_2$O | Sigma-Aldrich |
| RE2 | Neodymium (Nd) | c = 0.1 | Neodymium Nitrate: Nd(NO$_3$)$_3$•6H$_2$O | Sigma-Aldrich |
| AT = RE3 | Erbium (Er) | d = 0.3 | Erbium Nitrate Er(NO$_3$)$_3$•6H$_2$O | Sigma-Aldrich |

Method for preparing the composition containing the inventive catalyst of Example 2 ($Na_{0.3}Sr_{1.0}La_{0.5}$ $Nd_{0.1}Er_{0.3}O_x$): The composition containing the catalyst of Example 2, was prepared in the manner identical to that used for preparing Example 1.

For Example 2, specifically, the method included the step of obtaining the mixed metal oxide precursor containing 8.47 g of strontium nitrate ($Sr(NO_3)_2$), 8.66 g of lanthanum nitrate ($La(NO_3)_3 \cdot 6H_2O$), 1.76 g of neodymium nitrate ($Nd(NO_3)_3 \cdot 6H_2O$) and 5.32 g of erbium nitrate ($Er(NO_3)_3 \cdot 6H_2O$). The mixed metal oxide precursor was taken in a crucible and then blended with the alkali metal compound in the form of 1.02 g of sodium nitrate ($NaNO_3$). The rest of the procedure followed was same as that of Example 1, to obtain the inventive catalyst of Example 2.

Process for producing $C_{2+}$ hydrocarbon mixture product using the composition of Example 2: The composition obtained from the practice of Example 2, was thereafter used for producing $C_{2+}$ hydrocarbon mixture product using the process and conditions as described under Example 1. For Example 2, the $C_{2+}$ hydrocarbon selectivity was measured across a broad range of methane and oxygen conversion values during the course of the OCM reaction and the maximum value was noted. The performance of the inventive catalyst composition was compared with the performance of Reference 1 and Reference 2 catalyst composition.

Results: The catalyst performance of the inventive catalyst composition of Example 2, and catalyst performance obtained from the use of Reference 2 catalyst composition, is tabulated below.

TABLE 5

Catalyst selectivity/Activity ($Na_{0.3}Sr_{1.0}La_{0.5}Nd_{0.1}Er_{0.3}O_x$)

| | Maximum $C_{2+}$ hydrocarbon selectivity | Minimum carbon oxide ($CO_X$) selectivity |
| --- | --- | --- |
| Inventive composition Example 2 | 85.0 | 15.0 |
| (Control) Reference 1 - $Sr_{1.0}La_{0.5}Nd_{0.1}Er_{0.2}O_x$ | 79.8 | 20.2 |
| (Control) Reference 2 $Sr_{1.0}La_{0.5}Nd_{0.1}Er_{0.3}O_x$ | 79.7 | 20.3 |

The results from Table 5 indicate that inventive catalyst composition of Example 2, demonstrates over 6.6% improvement in the $C_{2+}$ hydrocarbon selectivity compared to the $C_{2+}$ hydrocarbon selectivity of the Reference 2 catalyst composition and about 6.5% compared to Reference 1. Accordingly, the inventive catalyst demonstrates reduced selectivity towards carbon oxide byproducts ($CO_X$) with a reduction in selectivity of about 26% compared to Reference 1 and Reference 2 catalyst composition. The increased selectivity towards the more useful $C_{2+}$ hydrocarbon products over that of carbon oxide byproducts, is particular beneficial in improving product yield and improving the overall OCM process efficiency. Further, it is expected that the methane conversion property and $C_{2+}$ hydrocarbon yield of the Example 2 composition should have similar level of performance as that of Example 1, owing to similar composition.

Example 3

Catalyst Composition Having the Formula ($Na_{0.7}Sr_{1.0}La_{0.5}Nd_{0.1}Er_{0.3}O_x$) Formed by Using Sodium Salt Precursor.

Purpose: Example 3 demonstrates the preparation and use of a composition comprising an alkali metal promoted catalyst, having the formula ($Na_{0.7}Sr_{1.0}La_{0.5}Nd_{0.1}Er_{0.3}O_x$). The incorporation of sodium in the catalyst composition is achieved by using a sodium nitrate salt as the precursor material. The performance of the inventive catalyst composition of Example 3 is compared with a control (Reference 1 and Reference 2 catalyst composition) containing a catalyst composition, which is free of sodium metal promoter.

Materials: The following materials are procured and used for the synthesis of the composition.

TABLE 6

Inventive catalyst composition ($Na_{0.7}Sr_{1.0}La_{0.5}Nd_{0.1}Er_{0.3}O_x$)

| Catalyst composition: $AM_zAE_aRE1_bRE2_cAT_dO_x$ | Element/ Compound used | Relative molar ratio | Precursor Material | Supplier |
| --- | --- | --- | --- | --- |
| AM | Sodium (Na) | z = 0.7 | Sodium Nitrate $Na(NO_3)$ | Sigma-Aldrich |
| AE | Strontium (Sr) | a = 1.0 | Strontium Nitrate: $Sr(NO_3)_2$ | Sigma-Aldrich |
| RE1 | Lanthanum (La) | b = 0.5 | Lanthanum Nitrate $La(NO_3)_3 \cdot 6H_2O$ | Sigma-Aldrich |
| RE2 | Neodymium (Nd) | c = 0.1 | Neodymium Nitrate: $Nd(NO_3)_3 \cdot 6H_2O$ | Sigma-Aldrich |
| AT = RE3 | Erbium (Er) | d = 0.3 | Erbium Nitrate $Er(NO_3)_3 \cdot 6H_2O$ | Sigma-Aldrich |

Method for preparing the composition containing the inventive catalyst of Example 3 ($Na_{0.7}Sr_{1.0}La_{0.5}Nd_{0.1}Er_{0.3}O_x$): The composition containing the inventive catalyst of Example 3, was prepared in the same manner as was done for Example 1.

For Example 3, specifically, the method included the step of obtaining the mixed metal oxide precursor containing 8.47 g of strontium nitrate ($Sr(NO_3)_2$), 8.66 g of lanthanum nitrate ($La(NO_3)_3 \cdot 6H_2O$), 1.76 g of neodymium nitrate ($Nd(NO_3)_3 \cdot 6H_2O$) and 5.32 g of erbium nitrate ($Er(NO_3)_3 \cdot 6H_2O$). The mixed metal oxide precursor was taken in a crucible and then blended with the alkali metal compound in the form of 2.38 g of sodium nitrate ($NaNO_3$). The rest of the method followed was identical to what was practiced for Example 1.

Process for producing $C_{2+}$ hydrocarbon mixture product using the composition of Example 3: The composition obtained from the practice of Example 3, was thereafter used for producing $C_{2+}$ hydrocarbon mixture product using the process and conditions identical to what was used for the inventive catalyst composition of Example 1.

Results: The catalyst performance obtained using the catalyst composition of Example 3 and catalyst performance obtained from the use of the catalyst composition of Reference 1 and Reference 2 catalyst compositions, are tabulated below.

sition of Example 4 is compared with a control which is free of sodium metal promoter (Reference 1 and Reference 2 catalyst composition).

Materials: The following materials were procured and was used for the synthesis of the composition.

TABLE 8

Inventive catalyst composition ($Na_{1.0}Sr_{1.0}La_{0.5}Nd_{0.1}Er_{0.3}O_x$)

| Catalyst composition: $AM_zAE_aRE1_bRE2_cAT_dO_x$ | Element/ Compound used | Relative molar ratio | Precursor Material | Supplier |
|---|---|---|---|---|
| AM | Sodium (Na) | z = 1.0 | Sodium Nitrate $Na(NO_3)$ | Sigma-Aldrich |
| AE | Strontium (Sr) | a = 1.0 | Strontium Nitrate: $Sr(NO_3)_2$ | Sigma-Aldrich |
| RE1 | Lanthanum (La) | b = 0.5 | Lanthanum Nitrate $La(NO_3)_3 \cdot 6H_2O$ | Sigma-Aldrich |
| RE2 | Neodymium (Nd) | c = 0.1 | Neodymium Nitrate: $Nd(NO_3)_3 \cdot 5H_2O$ | Sigma-Aldrich |
| AT = RE3 | Erbium (Er) | d = 0.3 | Erbium Nitrate $Er(NO_3)_3 \cdot 6H_2O$ | Sigma-Aldrich |

TABLE 7

Catalyst selectivity ($Na_{0.7}Sr_{1.0}La_{0.5}Nd_{0.1}Er_{0.3}Ox$)

| | Maximum $C_{2+}$ hydrocarbon selectivity | Minimum carbon oxide ($CO_X$) selectivity |
|---|---|---|
| Inventive composition Example 3 | 84.3 | 15.7 |
| (Control) Reference 1 - $Sr_{1.0}La_{0.5}Nd_{0.1}Er_{0.2}O_x$ | 79.8 | 20.2 |
| (Control) Reference 2 $Sr_{1.0}La_{0.5}Nd_{0.1}Er_{0.3}O_x$ | 79.7 | 20.3 |

The results from Table 7 indicate that inventive catalyst composition of Example 3, demonstrates about 5.6% improvement in the $C_{2+}$ hydrocarbon selectivity compared to the $C_{2+}$ hydrocarbon selectivity of both Reference 1 and Reference 2 catalyst composition. Accordingly, the inventive catalyst demonstrates reduced selectivity towards carbon oxide byproducts ($CO_X$) with a reduction in $CO_X$ selectivity of over 22% compared to Reference 1 catalyst composition. The increased selectivity towards the more useful $C_{2+}$ hydrocarbon products over that of carbon oxide byproducts, is particular beneficial in improving product yield and improving the overall OCM process efficiency. Further, it is expected that the methane conversion and $C_{2+}$ hydrocarbon yield property of the inventive composition of Example 3, should have similar level of performance as that of Example 1, owing to similar composition.

Example 4

Catalyst Composition Having the Formula ($Na_{1.0}Sr_{1.0}La_{0.5}Nd_{0.1}Er_{0.3}O_x$) Formed by Using Sodium salt precursor.

Purpose: Example 4 demonstrates the preparation and use of a composition comprising an alkali metal promoted catalyst, having the formula ($Na_{1.0}Sr_{1.0}La_{0.5}Nd_{0.1}Er_{0.3}O_x$). The incorporation of sodium in the catalyst composition is achieved by using a sodium nitrate salt as the precursor material. The performance of the inventive catalyst compo- Method for preparing the composition containing the inventive catalyst of Example 4 ($Na_{1.0}Sr_{1.0}La_{0.5}Nd_{0.1}Er_{0.3}O_x$): The composition containing the catalyst of Example 4, was prepared in the same manner as was done for Example 1.

For Example 4, specifically, the method included the step of obtaining the mixed metal oxide precursor containing 4.23 g of strontium nitrate ($Sr(NO_3)_2$), 4.33 g of lanthanum nitrate ($La(NO_3)_{3.6}H_2O$), 0.88 g of neodymium nitrate ($Nd(NO_3)_{3.6}H_2O$) and 2.66 g of erbium nitrate ($Er(NO_3)_{3.6}H_2O$). The mixed metal oxide precursor was taken in a crucible and then blended with the alkali metal compound in the form of 1.7 g of sodium nitrate ($Na(NO_3)$). The rest of the procedure followed was same as that of Example 1, to obtain the inventive catalyst composition of Example 4.

Process for producing $C_{2+}$ hydrocarbon mixture product using the composition of Example 4: The catalyst composition obtained from the practice of Example 4, was thereafter used for producing $C_{2+}$ hydrocarbon mixture product using the process and conditions identical to what was used for the inventive catalyst composition of Example 1.

Results: The catalyst performance obtained using the catalyst composition of Example 4 and catalyst performance obtained from the use of the catalyst composition of Reference 1 and Reference 2 catalyst compositions, are tabulated below.

TABLE 9

Catalyst selectivity ($Na_{1.0}Sr_{1.0}La_{0.5}Nd_{0.1}Er_{0.3}O_x$)

| | Maximum $C_{2+}$ hydrocarbon selectivity | Minimum carbon oxide ($CO_X$) selectivity |
|---|---|---|
| Inventive composition Example 4 | 83.0 | 17.0 |
| (Control) Reference 1 - $Sr_{1.0}La_{0.5}Nd_{0.1}Er_{0.2}O_x$ | 79.8 | 20.2 |
| (Control) Reference 2 $Sr_{1.0}La_{0.5}Nd_{0.1}Er_{0.3}O_x$ | 79.7 | 20.3 |

The results from Table 9 indicate that inventive catalyst composition of Example 4, demonstrates about 4% improvement in the $C_{2+}$ hydrocarbon selectivity compared to the $C_{2+}$ hydrocarbon selectivity of the Reference 1 and Reference 2 catalyst composition. Accordingly, the inventive catalyst demonstrates reduced selectivity towards carbon oxide byproducts ($CO_X$) with a reduction in $CO_X$ selectivity of over 19%. The increased selectivity towards the more useful $C_{2+}$ hydrocarbon products over that of carbon oxide byproducts, is particular beneficial in improving product yield and improving the overall OCM process efficiency. Further it is expected that the methane conversion and $C_{2+}$ hydrocarbon yield property of the inventive composition of Example 4, should have similar level of performance as that of Example 1, owing to similar composition.

Example 5

Catalyst Composition Having the Formula ($Na0.1Sr1.0La0.5Nd0.1Er0.3O_x$) Formed by Using Sodium Salt Precursor.

Purpose: Example 5 demonstrates the preparation and use of a composition comprising an alkali metal promoted catalyst, having the formula ($Na_{0.1}Sr_{1.0}La_{0.5}Nd_{0.1}Er_{0.3}O_x$). The incorporation of sodium in the catalyst composition is achieved by using a sodium nitrate salt as the precursor material. The performance of the inventive catalyst composition of Example 5 is compared with a control, which is free of sodium metal promoter (Reference 1 and Reference 2 catalyst composition).

Materials: The following materials are procured and used for the synthesis of the composition.

TABLE 10

Inventive catalyst composition ($Na_{0.1}Sr_{1.0}La_{0.5}Nd_{0.1}Er_{0.3}O_x$)

| Catalyst composition: $AM_zAE_aRE1_bRE2_cAT_dO_x$ | Element/ Compound used | Relative molar ratio | Precursor Material | Supplier |
|---|---|---|---|---|
| AM | Sodium (Na) | z = 0.1 | Sodium Nitrate $Na(NO_3)$ | Sigma-Aldrich |
| AE | Strontium (Sr) | a = 1.0 | Strontium Nitrate $Sr(NO_3)_2$ | Sigma-Aldrich |
| RE1 | Lanthanum (La) | b = 0.5 | Lanthanum Nitrate $La(NO_3)_3 \cdot 6H_2O$ | Sigma-Aldrich |
| RE2 | Neodymium (Nd) | c = 0.1 | Neodymium Nitrate $Nd(NO_3)_3 \cdot 6H_2O$ | Sigma-Aldrich |
| AT = RE3 | Erbium (Er) | d = 0.3 | Erbium Nitrate $Er(NO_3)_3 \cdot 6H_2O$ | Sigma-Aldrich |

Method for preparing the composition containing the inventive catalyst of Example 5 ($Na_{0.1}Sr_{1.0}La_{0.5}Nd_{0.1}Er_{0.3}O_x$): The composition containing the catalyst of Example 5, was prepared in the same manner as was done for Example 1.

For Example 5, specifically, the method included the step of obtaining the mixed metal oxide precursor containing 8.47 g of strontium nitrate ($Sr(NO_3)_2$), 8.66 g of lanthanum nitrate ($La(NO_3)_{3.6}H_2O$), 1.76 g of neodymium nitrate ($Nd(NO_3)_{3.6}H_2O$) and 5.32 g of erbium nitrate ($Er(NO_3)_{3.6}H_2O$). The mixed metal oxide precursor was taken in a crucible and then blended with the alkali metal compound in the form of 0.34 g of sodium nitrate ($Na(NO_3)$). The rest of the procedure followed was same as that of Example 1, to obtain the inventive catalyst composition of Example 5.

Process for producing $C_{2+}$ hydrocarbon mixture product using the composition of Example 5: The catalyst composition obtained from the practice of Example 5, was thereafter used for producing $C_{2+}$ hydrocarbon mixture product, using the process and conditions identical to what was used for the inventive catalyst composition of Example 1.

Results: The catalyst performance obtained using the catalyst composition of Example 5 and catalyst performance obtained from the use of the catalyst composition of Reference 1 and Reference 2, are tabulated below.

TABLE 11

Catalyst selectivity/Activity ($Na_{0.1}Sr_{1.0}La_{0.5}Nd_{0.1}Er_{0.3}O_x$)

| | Maximum $C_{2+}$ hydrocarbon selectivity | Minimum carbon oxide ($CO_X$) selectivity |
|---|---|---|
| Inventive composition Example 5 | 82.2 | 17.8 |
| (Control) Reference 1 - $Sr_{1.0}La_{0.5}Nd_{0.1}Er_{0.2}O_x$ | 79.8 | 20.2 |
| (Control) Reference 2 $Sr_{1.0}La_{0.5}Nd_{0.1}Er_{0.3}O_x$ | 79.7 | 20.3 |

The results from Table 11 indicate that inventive catalyst composition of Example 5, demonstrates over 4% improvement in the $C_{2+}$ hydrocarbon selectivity compared to the $C_{2+}$ hydrocarbon selectivity of the Reference 1 and Reference 2 catalyst composition. Accordingly, the inventive catalyst demonstrates reduced selectivity towards carbon oxide byproducts ($CO_X$) with a reduction in $CO_X$ selectivity of over 15%. The increased selectivity towards the more useful $C_{2+}$ hydrocarbon products over that of carbon oxide byproducts, is particular beneficial in improving product yield and improving the overall OCM process efficiency. Further it is expected that the methane conversion and yield property of the inventive composition of Example 5, should have similar level of performance as that of Example 1, owing to similar composition.

Example 6

Catalyst Composition Having the Formula (($Na2WO4$)$0.5Sr1.0La0.5Nd0.1Er0.3O_x$) Formed by Using Sodium Tungstate Precursor.

Purpose: Example 6 demonstrates the preparation and use of a composition comprising an alkali metal tungstate promoted catalyst, having the formula (($Na_2WO_4)_{0.5}Sr_{1.0}La_{0.5}Nd_{0.1}Er_{0.3}O_x$). The catalytic performance of the inventive composition of Example 6 is compared with a control which is free of sodium metal promoter (Reference 1 and Reference 2 catalyst composition).

Materials: The following materials are procured and used for the synthesis of the composition.

TABLE 12

Inventive catalyst composition $((Na_2WO_4)_{0.5}Sr_{1.0}La_{0.5}Nd_{0.1}Er_{0.3}O_x)$

| Catalyst composition: $AM_zAE_aRE1_bRE2_cAT_dO_x$ | Element/ Compound used | Relative molar ratio | Precursor Material | Supplier |
|---|---|---|---|---|
| AM | Sodium Tungstate $(Na_2WO_4 \cdot 6H_2O)$ | z = 0.5 | Sodium Nitrate $Na(NO_3)$ | Sigma-Aldrich |
| AE | Strontium (Sr) | a = 1.0 | Strontium Nitrate $Sr(NO_3)_2$ | Sigma-Aldrich |
| RE1 | Lanthanum (La) | b = 0.5 | Lanthanum Nitrate $La(NO_3)_3 \cdot 6H_2O$ | Sigma-Aldrich |
| RE2 | Neodymium (Nd) | c = 0.1 | Neodymium Nitrate $Nd(NO_3)_3 \cdot 6H_2O$ | Sigma-Aldrich |
| AT = RE3 | Erbium (Er) | d = 0.3 | Erbium Nitrate $Er(NO_3)_3 \cdot 6H_2O$ | Sigma-Aldrich |

Method for preparing the composition containing the inventive catalyst of Example 6 $((Na_2WO_4)_{0.5}Sr_{1.0}La_{0.5}Nd_{0.1}Er_{0.3}O_x)$: The composition containing the catalyst of Example 6, was prepared by a general method of (i) blending an alkali metal compound and a mixed metal oxide precursor and forming a catalyst precursor mixture, and (ii) calcining the catalyst precursor mixture at a temperature of at least 850° C. for at least 5 hours and forming the composition containing the catalyst of Example 6. For the purpose of Example 6, both the mixed metal oxide precursor and the alkali metal compound were each independently calcined at a temperature of at least 300° C. for at least 3 hours, prior to forming the catalyst precursor mixture.

More specifically, the method included the step of obtaining the mixed metal oxide precursor containing 4.23 g of strontium nitrate $(Sr(NO_3)_2)$, 4.33 g of lanthanum nitrate $(La(NO_3)_{3.6}H_2O)$, 0.88 g of neodymium nitrate $(Nd(NO_3)_{3.6}H_2O)$ and 2.66 g of erbium nitrate $(Er(NO_3)_{3.6}H_2O)$. The mixed metal oxide precursor was taken in a crucible and thoroughly mixed and dissolved using 40 ml of distilled water. Subsequently, the crucible was placed in a drying oven for drying overnight at 120° C. followed by calcining the mixed metal oxide precursor at 500° C. for 6 hours. Independently, 3.3 g of the alkali metal compound in the form of sodium tungstate was calcined at 300° C. for 3 hours and the resultant calcined sodium tungstate compound was blended with the calcined mixed metal oxide precursor to form the catalyst precursor mixture. The catalyst precursor mixture was subsequently calcined at 900° C. for 6 hours to obtain the inventive catalyst composition of Example 6.

The key difference in the method of preparation of catalyst composition of Example 6, with the method practiced for the other inventive compositions (Example 1-5), is that each of the mixed metal oxide precursor and the alkali metal compound were independently calcined prior to forming the catalyst precursor mixture.

Inventive composition of Example 6(a) $((Na_2WO_4)_{0.5}Sr_{1.0}La_{0.5}Nd_{0.1}Er_{0.3}O_x)$: An alternative approach to prepare the inventive catalyst composition of Example 6 $((Na_2WO_4)_{0.5}Sr_{1.0}La_{0.5}Nd_{0.1}Er_{0.3}O_x)$ involves, obtaining a mixed metal oxide precursor containing 4.23 g of strontium nitrate $(Sr(NO_3)_2)$, 4.33 g of lanthanum nitrate $(La(NO_3)_{3.6}H_2O)$, 0.88 g of neodymium nitrate $(Nd(NO_3)_{3.6}H_2O)$ and 2.66 g of erbium nitrate $(Er(NO_3)_{3.6}H_2O)$. The mixed metal oxide precursor was taken in a crucible and thoroughly mixed and dissolved using 40 ml of distilled water. The crucible containing the mixed metal precursor was placed in a drying oven overnight at 120° C. Subsequently, 3.3 g of sodium tungstate was blended with the dried mixed metal oxide precursor to obtain the catalyst precursor mixture. The catalyst precursor mixture was subsequently calcined at 900° C. for 6 hours to obtain the inventive catalyst composition of Example 6 (a). The key difference in the method of preparation of Example 6 and Example 6(a), is that in Example 6, the precursor mixed metal oxide and alkali metal compound (sodium tungstate) were both independently calcined prior to forming the catalyst precursor mixture whereas for Example 6(a) the mixed metal oxide precursor and the alkali metal compound were first blended to form the catalyst precursor mixture and subsequently the catalyst precursor mixture was calcined.

Process for producing $C_{2+}$ hydrocarbon mixture product using the composition of Example 6 or Example 6(a): The composition obtained from the practice of Example 6 and Example 6(a), was thereafter used for producing $C_{2+}$ hydrocarbon mixture product using the process and condition parameters identical to any of the process described under Examples 1-5.

Results: The catalyst performance obtained using the catalyst composition of Example 6 and Example 6(a), was compared with the performance of Reference 1 and Reference 2 catalyst compositions, and the results are tabulated below.

TABLE 13

Catalyst selectivity

| | Maximum $C_{2+}$ hydrocarbon selectivity | Minimum carbon oxide $(CO_X)$ selectivity |
|---|---|---|
| Inventive composition Example 6 | 84.8 | 15.2 |
| Inventive composition Example 6(a) | 83.1 | 16.9 |
| (Control) Reference 1 - $Sr_{1.0}La_{0.5}Nd_{0.1}Er_{0.3}O_x$ | 79.8 | 20.2 |
| (Control) Reference 2 $Sr_{1.0}La_{0.5}Nd_{0.1}Er_{0.3}O_x$ | 79.7 | 20.3 |

The results from Table 13 indicate that inventive catalyst composition of Example 6, demonstrates about 6% improvement in the $C_{2+}$ hydrocarbon selectivity compared to the $C_{2+}$ hydrocarbon selectivity of the Reference 1 and Reference 2 catalyst composition. For the composition of Example 6(a), the catalyst composition demonstrates over 4% increase in the $C_{2+}$ hydrocarbon selectivity compared to the $C_{2+}$ hydrocarbon selectivity of Reference 1 and Reference 2 catalyst composition. Accordingly, for both catalyst compositions, Example 6 and Example 6(a), the selectivity towards byproduct carbon oxides ($CO_x$) were significantly reduced compared to the Reference 1 or Reference 2 catalyst compositions.

Example 7 (Comparative)

Catalyst composition having the formula $(Sr_1La_{0.4}Er_{0.4}Nd_{0.1}O_x)_{0.25}$—$(Na_2WO_4/SiO_2)_{0.75}$ with first catalyst component present in an amount of 25 wt. % and the second catalyst component present in an amount of 75 wt. %.

Purpose: Example 7 demonstrates the use of a composition comprising a catalyst having the formula $(Sr_1La_{0.4}Er_{0.4}Nd_{0.1}O_x)_{0.25}$—$(Na_2WO_4/SiO_2)_{0.75}$. The purpose of this example is to demonstrate the effect of using a silica supported sodium tungstate promoter blended with a mixed metal oxide component, and compare the results with that of inventive composition of Example 6.

Preparation: Physical blending of 2.5 g of the catalyst component $(Sr_1La_{0.4}Er_{0.4}Nd_{0.1}O_x)$ with 7.5 g of the catalyst component $(Na_2WO_4/SiO_2)$ followed by grinding and press sizing the resulting blend.

Process for producing $C_{2+}$ hydrocarbon mixture product using the composition of Example 7: The composition obtained from the practice of Example 7 was used for producing $C_{2+}$ hydrocarbon mixture product using the process and operating parameters as described under Example 6. The results for $C_{2+}$ hydrocarbon selectivity was subsequently compared with Example 6. The conditions used for testing and measuring of the results are identical to what has been disclosed under the procedure of Example 1.

Results: The results are provided in the table below in comparison with Example 6 inventive composition:

TABLE 14

Catalyst selectivity $(Sr_1La_{0.4}Er_{0.4}Nd_{0.1}O_x)_{0.25}$—$(Na_2WO_4/SiO_2)_{0.75}$

|  | Maximum $C_{2+}$ hydrocarbon selectivity | Minimum carbon oxide ($CO_X$) selectivity |
|---|---|---|
| Comparative example composition Example 7 | 80.3 | 19.7 |

TABLE 14-continued

Catalyst selectivity $(Sr_1La_{0.4}Er_{0.4}Nd_{0.1}O_x)_{0.25}$—$(Na_2WO_4/SiO_2)_{0.75}$

|  | Maximum $C_{2+}$ hydrocarbon selectivity | Minimum carbon oxide ($CO_X$) selectivity |
|---|---|---|
| Inventive composition Example 6 | 84.8 | 15.2 |

The results indicate that the composition of Example 6 obtained as an embodiment of the present invention, demonstrates improved $C_{2+}$ hydrocarbon selectivity over that of the comparative Example 7. The effect of calcining the unsupported sodium tungstate promoter with the mixed metal oxide precursor, is that of improved $C_{2+}$ hydrocarbon selectivity with low selectivity towards carbon oxide byproducts.

Summary—From the example section it is evident that the composition containing the catalyst of the present invention, demonstrates improved selectivity towards $C_{2+}$ hydrocarbons compared to a similar catalyst compositions (Reference 1 or Reference 2) which are free of alkali metal or alkali metal tungstate promoters. As is evident from Table 15 below, with an increase in the relative molar ratio of sodium metal promoter, the selectivity towards $C_{2+}$ hydrocarbon increases steadily to a certain level and thereafter starts decreasing. Therefore, as may be appreciated by a person skilled in the art, selectivity towards $C_{2+}$ hydrocarbons may be maximized by incorporating only specific amounts of alkali metal promoters relative to other catalyst components.

Results from Example 7 further demonstrates, improved $C_{2+}$ hydrocarbon selectivity over catalyst compositions, which are supported with silica and formed by physical blending of alkali metal promoters and mixed metal oxide. Further, the methane conversion and $C_{2+}$ hydrocarbon yield of Example 1, when compared with that of Reference 1 catalyst composition, demonstrates nearly 16% improvement in methane conversion and nearly 40% improvement in the $C_{2+}$ hydrocarbon yield. Accordingly, by way of inventive examples (Example 1-6) as embodiments of the present example, it is evident that the catalyst composition of the present invention demonstrates excellent $C_{2+}$ hydrocarbon selectivity, improved methane conversion and improved $C_{2+}$ hydrocarbon yield, thereby resulting in improved product yield and overall process efficiency for the conversion of methane to commercially useful $C_{2+}$ hydrocarbon products.

TABLE 15

Summary Catalyst selectivity/Methane conversion/Yield

|  | Composition | $C_{2+}$ hydrocarbon selectivity (%) | % Increase in $C_{2+}$ hydrocarbon selectivity from Reference 2 | % Increase in methane conversion at 40% $O_2$ conversion, over Reference 1 | % Increase $C_{2+}$ hydrocarbon yield at 40% $O_2$ conversion over Reference 1 |
|---|---|---|---|---|---|
| (Comparative) Reference 1 | $Sr_{1.0}La_{0.5}Nd_{0.1}Er_{0.2}O_x$ | 79.8 | NA | — | — |
| (Comparative) Reference 2 | $Sr_{1.0}La_{0.5}Nd_{0.1}Er_{0.3}O_x$ | 79.7 | — | NA | NA |
| Example 1 | $Na_{0.5}Sr_{1.0}La_{0.5}Nd_{0.1}Er_{0.3}O_x$ | 85.4 | 7.15% | 15.9% | 39.5% |
| Example 2 | $Na_{0.3}Sr_{1.0}La_{0.5}Nd_{0.1}Er_{0.3}O_x$ | 85.0 | 6.65% | NA | NA |
| Example 3 | $Na_{0.7}Sr_{1.0}La_{0.5}Nd_{0.1}Er_{0.3}O_x$ | 84.3 | 5.77% | NA | NA |
| Example 4 | $Na_{1.0}Sr_{1.0}La_{0.5}Nd_{0.1}Er_{0.3}O_x$ | 83.0 | 4.14% | NA | NA |
| Example 5 | $Na_{0.1}Sr_{1.0}La_{0.5}Nd_{0.1}Er_{0.3}O_x$ | 82.2 | 3.13% | NA | NA |
| Example 6 | $(Na_2WO_4)_{0.5}Sr_{1.0}La_{0.5}Nd_{0.1}Er_{0.3}O_x$ | 84.8 | 6.4% | NA | NA |
| Example 6(a) | $(Na_2WO_4)_{0.5}Sr_{1.0}La_{0.5}Nd_{0.1}Er_{0.3}O_x$ | 83.1 | 4.27% | NA | NA |

TABLE 15-continued

Summary Catalyst selectivity/Methane conversion/Yield

| Composition | | $C_{2+}$ hydrocarbon selectivity (%) | % Increase in $C_{2+}$ hydrocarbon selectivity from Reference 2 | % Increase in methane conversion at 40% $O_2$ conversion, over Reference 1 | % Increase $C_{2+}$ hydrocarbon yield at 40% $O_2$ conversion over Reference 1 |
|---|---|---|---|---|---|
| (Comparative) Example 7 | $(Sr_1La_{0.4}Er_{0.4}Nd_{0.1}O_x)_{0.25}$—$(Na_2WO_4/SiO_2)_{0.75}$ | 80.3 | NA | NA | NA |

The invention claimed is:

1. A composition, comprising a catalyst represented by a general formula (I): $(AM_zAE_aRE 1_bRE2_cAT_dO_x)$
wherein,
(i) 'AM' represents any one of an alkali metal or an alkali metal tungstate, wherein the alkali metal is selected from the group consisting of sodium, potassium, rubidium and caesium and wherein the alkali metal tungstate is selected from the group consisting of sodium tungstate, potassium tungstate, rubidium tungstate and caesium tungstate;
(ii) 'AE' represents an alkaline earth metal;
(iii) 'RE1' represents a first rare earth element;
(iv) 'RE2' represents a second rare earth element; and
(v) 'AT' represents a third rare earth element 'RE3', or a redox agent 'RX' selected from antimony, tin, nickel, chromium, molybdenum, tungsten, manganese, bismuth; wherein, 'a', 'b', 'c', 'd' and 'z' each independently represent relative molar ratio; wherein 'a' is 1.0; 'b' ranges from about 0.1 to about 10; 'c' ranges from 0 to about 10; 'd' ranges from 0 to about 10; 'z' ranges from about 0.01 to about 2; 'x' balances the oxidation state; wherein, the first rare earth element, the second rare earth element and the third rare earth element, are different; and wherein further the catalyst is unsupported by silica.

2. The composition of claim 1, wherein the relative molar ratio 'z' ranges from about 0.3 to about 1.

3. The composition of claim 1, wherein the relative molar ratio 'a' is 1.0, relative molar ratio 'b' is 0.5, relative molar ratio 'c' is 0.1 and the relative molar ratio 'd' is 0.3.

4. The composition of claim 1, wherein the alkali metal is sodium.

5. The composition of claim 1, wherein the alkali metal tungstate is sodium tungstate.

6. The composition of claim 1, wherein the alkaline earth metal 'AE' is selected from the group consisting of magnesium, calcium, strontium, barium, and combinations thereof.

7. The composition of claim 6, wherein the alkaline earth metal 'AE' is strontium.

8. The composition of claim 1, wherein the first rare earth element 'RE1', the second rare earth element 'RE2', and the third rare earth element 'RE3', are each independently selected from the group consisting of lanthanum, scandium, cerium, praseodymium, neodymium, promethium, samarium, europium, gadolinium, yttrium, terbium, dysprosium, holmium, erbium, thulium, ytterbium, lutetium, and combinations thereof.

9. The composition of claim 1, wherein the alkaline earth metal 'AE' is strontium, the first rare earth element 'RE1' is lanthanum, the second rare earth element 'RE2' is neodymium, and the third rare earth element 'RE3' is erbium.

10. The composition of claim 1, wherein the catalyst of formula (I) is represented by a general formula $Na_zSr_aLa_bNd_cEr_dO_x$, wherein 'a' is 1.0; 'z' ranges from about 0.09 to about 1.0; 'b' ranges from about 0.3 to about 1; 'c' ranges from greater than zero to about 0.3; and 'd' ranges from about greater than zero to about 0.5.

11. The composition of claim 1, wherein the catalyst of formula (I) is represented by the formula $Na0.3Sr1.0La0.5Nd0.1Er0.3O_x$.

12. The composition of claim 1, wherein the catalyst of formula (I) is represented by the formula $Na0.5Sr1.0La0.5Nd0.1Er0.3O_x$.

13. The composition of claim 1, wherein the composition has a C2+ hydrocarbon selectivity ranging from about 82% to about 93% of total product formed, when the composition is used in a process for producing C2+ hydrocarbon from methane and oxygen.

14. A method for preparing the composition of claims 1, the method comprising: (i) blending an alkali metal compound and a mixed metal oxide precursor and forming a catalyst precursor mixture; wherein the mixed metal oxide precursor comprises: a compound containing an alkaline earth metal 'AE' and at least one compound containing a first rare earth element 'RE1'; wherein the metal oxide precursor optionally comprises a compound containing a second rare earth element 'RE2' and/or a compound containing a third rare earth element 'RE3' or a redox agent 'RX'; and wherein the catalyst precursor mixture is characterized by a molar ratio of alkali metal compound to AE of from about 0.01 to about 2, a molar ratio of REa to AE of from about 0.1 to about 10, a molar ratio of RE2 to AE of from 0 to about 10, and a molar ratio of RE3 or RX to AE of from 0 to about 10; and (ii) calcining the catalyst precursor mixture at a temperature of at least 850° C. and for at least 5 hours and forming the composition of claim 1.

15. The method of claim 14, wherein each of the mixed metal oxide precursor and the alkali metal compound, is independently calcined at a temperature of at least 300° C. and for at least 3 hours, prior to step (i).

16. The method of claim 14, wherein the mixed metal oxide precursor and the alkali metal compound are dissolved in water to form an aqueous catalyst precursor solution prior to step (i).

17. The method of claim 16 further comprising drying at least a portion of the aqueous catalyst precursor solution at a temperature of at least about 110° C. to form the catalyst precursor mixture.

18. A process for producing a $C_{2+}$ hydrocarbon mixture product, comprising:
(a) introducing a feed mixture comprising methane and oxygen in a reactor containing the composition of claim 1;
(b) subjecting the feed mixture to a methane coupling reaction under conditions suitable to produce the C2+ hydrocarbon mixture product; and (c) recovering the C2+ hydrocarbon mixture product after removing unconverted methane from the C2+ hydrocarbon mixture product.

19. The process of claim 18, wherein the feed mixture has a molar ratio of methane to oxygen ranging from about 2:1 to about 15:1.

20. The composition of claim 1, wherein the catalyst of formula (I) is represented by a general formula $AM_zSr_aLa_bRE2_cAT_dO_x$, wherein 'a' is 1.0; 'z' ranges from about 0.09 to about 1.0; 'b' ranges from about 0.3 to about 1; 'c' ranges from greater than zero to about 0.3; and 'd' ranges from about greater than zero to about 0.5.

* * * * *